United States Patent [19]

Drehman

[11] 4,152,365

[45] May 1, 1979

[54] SELECTIVE HYDROGENATION OF POLYENES

[75] Inventor: Lewis E. Drehman, Bartlesville, Okla.

[73] Assignee: Phillips Petroleum Company, Bartlesville, Ohio

[21] Appl. No.: 559,180

[22] Filed: Mar. 17, 1975

[51] Int. Cl.$^2$ .................. C07C 11/02; C10G 39/00; C10G 23/00

[52] U.S. Cl. .................................. 585/256; 208/66; 208/135;; 208/137; 208/138; 208/143; 585/262; 585/313; 585/660; 585/671

[58] Field of Search ............ 208/66, 143; 260/677 H, 260/683.9

[56] References Cited

U.S. PATENT DOCUMENTS

| | | | |
|---|---|---|---|
| 2,426,870 | 9/1947 | Hill | 260/683.9 |
| 2,608,534 | 8/1952 | Fleck | 260/683.9 |
| 3,309,307 | 3/1967 | Bryant | 208/144 |
| 3,446,865 | 5/1969 | Roth et al. | 260/683.9 |
| 3,457,163 | 7/1969 | Parker | 208/255 |
| 3,641,182 | 2/1972 | Box et al. | 260/680 R |
| 3,883,418 | 5/1975 | Drehman et al. | 208/66 |

*Primary Examiner*—Herbert Levine

[57] ABSTRACT

A feedstock comprising olefinic hydrocarbons having more than one double bond per molecule is selectively hydrogenated to produce hydrocarbons having less unsaturation relative to the feedstock by contacting the feedstock in the presence of steam and hydrogen with a catalyst comprising a Group VIII metal or an oxide thereof on a carrier comprising a Group II metal aluminate spinel containing tin or an oxide of tin. The feedstock can be produced by reforming paraffin and cycloparaffin hydrocarbons in the presence of steam with a catalyst comprising a Group VIII metal or an oxide thereof on a carrier comprising a Group II metal aluminate spinel containing tin or an oxide of tin.

10 Claims, No Drawings

SELECTIVE HYDROGENATION OF POLYENES

BACKGROUND OF THE INVENTION

The invention relates to a process for selectively hydrogenating an olefinic hydrocarbon having more than one double bond per molecule. In another aspect, the invention relates to a process for reforming paraffin and cycloparaffin hydrocarbons to produce olefinic hydrocarbons having more than one double bond per molecule and selectively hydrogenating the olefinic hydrocarbons produced by said reforming process. In another aspect the invention relates to a process for the production of high octane gasoline from a feedback comprising paraffins and cycloparaffins.

In the production of non-leaded high octane gasoline from a feedback comprising paraffins and cycloparaffins by steam active reforming and subsequent selective hydrogenation of the reformate to reduce the unsaturation thereof, previously known selective hydrogenation catalysts require a relatively dry feed. Thus, the steam must be removed from the reformate, which usually involves a cooling step to condense the steam to water, a separation step to remove the water from the reformate and a reheating step to reheat the reformate to the desired selective hydrogenation temperature. Therefore, if a selective hydrogenation catalyst could be found wherein the reformate could be hydrotreated in the presence of steam, a substantial savings in equipment and energy could be realized.

It is an object of the invention to selectively hydrogenate olefinic hydrocarbons having more than one double bond per molecule.

Another object of the invention is to selectively hydrogenate olefinic hydrocarbons having more than one double bond per molecule over a catalyst in the presence of steam.

Yet another object of the invention is to reform paraffins and cycloparaffins in the presence of steam and then selectively hydrogenate the olefinic hydrocarbons having more than one double bond per molecule to reduce the unsaturation thereof without the removal of steam.

Other objects, aspects and advantages of the invention will be apparent to those skilled in the art after studying the specification and attached claims.

SUMMARY

In accordance with the present invention a feedstock comprising an olefinic hydrocarbon having more than one double bond per molecule is contacted with a catalyst in the presence of steam and hydrogen and under hydrogenating conditions to produce hydrocarbons having less unsaturation relative to the feedstock wherein the catalyst comprises a Group VIII metal or an oxide thereof on a carrier comprising a Group II metal aluminate spinel containing tin or an oxide of tin.

Further according to the invention, a feedstock is contacted with a first catalyst in a first zone in the presence of steam under conditions to reform the feedstock, the feedstock comprising paraffin and cycloparaffin hydrocarbons and the first catalyst comprising a Group VIII metal or an oxide thereof on a carrier comprising a Group II metal aluminate spinel containing tin or an oxide of tin and the reformate is contacted with a second catalyst in a second zone in the presence of steam and hydrogen and under hydrogenating conditions to selectively hydrogenate the polyenes contained in said reformate to reduce the unsaturation thereof, the second catalyst comprising a Group VIII metal or an oxide thereof on a carrier comprising a Group II metal aluminate spinel containing tin or an oxide of tin.

DETAILED DESCRIPTION OF THE INVENTION

The hydrocarbon feedstocks suitable for reforming and subsequently selectively hydrogenating in accordance with the present invention are those comprising paraffins and cycloparaffins. Generally, the paraffin and cycloparaffins contain from about 6 to about 20 carbon atoms per molecule; however, hydrocarbons having from about 6 to about 12 carbon atoms per molecule are of greater commercial importance and are preferred.

Examples of suitable paraffins and cycloparaffins are hexanes, heptanes, octanes, dodecanes, some octadecanes, eicosanes, methylcyclopentane, cyclohexane, cycloheptane, and the like, and mixtures thereof.

With regard to suitable feedstocks for selective hydrogenation in accordance with the present invention, olefinic hydrocarbons having more than one double bond per molecule are suitable. In general, any polyene can be selectively hydrogenated to produce a hydrocarbon of lower unsaturation by the process of this invention. As a matter of practical commercial application, polyenes having up to about 20 carbon atoms per molecule are most often selectively hydrogenated according to the invention. Some examples of these are 1,3-pentadiene, 1,5-cyclooctadiene, 1,3,7-octatriene, 4-vinylcyclohexene, 1,4,9-decatriene, 1,5,9-cyclododecatriene, 3,4-dimethyl-1,6-tridecadiene, and the like and mixtures thereof.

The catalysts employed in both the reforming and the selective hydrogenation zones in accordance with the invention comprise at least one Group VIII metal or metal compound capable of reduction in combination with tin or a compound of tin. All the Group VIII metals or metal compounds thereof are supported on a Group II metal aluminate spinel. Suitable Group VIII metals include for example nickel, platinum, ruthenium, palladium, iridium, osmium, or mixtures thereof. Platinum and palladium have been used with good results and these elements are preferred. Of the Group II elements useful in the carrier or support, good results have been obtained using zinc; thus zinc aluminate spinels are preferred. The Group VIII metal content of the catalyst varies widely. Generally the Group VIII metal content will range from about 0.1 to about 5 weight percent based on weight of support, but good results have been obtained employing a range of from about 0.1 to about 1 weight percent of support. In addition to the Group VIII metals other elements can be incorporated on the support. For example, the catalyst compositions can include activating components such as Group I-A and II-A metal compounds. The amount of the Group I-A or II-A compound or combination of compounds varies widely, but generally it is in the range of from about 0.5 to about 10 weight percent of support. Throughout the specification the term "weight percent of support" means parts by weight per 100 parts by weight of support.

The groups of metals referred to herein are as classified in the Periodic Table published in the Chemical Rubber Company's Handbook of Chemistry and Physics, 45th Edition (1964), page B-2.

In preparing the catalyst used in accordance with the present invention, it is important that the tin compound be incorporated with the support material prior to calcination of the support. The tin compound can be added to the support material in any suitable manner, such as deposition from solution, ball mill mixing, volatilization, plasma spraying, and the like. When added to the support from solution, the tin compounds can be deposited from aqueous solution or from nonaqueous solvents such as alcohols, hydrocarbons, ethers, ketones, and the like. Regardless of the manner of application, the particular tin compounds selected should have the capability of being convertible to either the stannous or stannic oxide form or to elemental tin, as by conversion during calcination. Among the tin compounds which can be employed as a source for the tin or tin oxide in the support composition of this invention are the halides, nitrates, oxalates, acetates, propionates, tartrates, hydroxides, and the like. The use of stannous halides is particularly effective and convenient. The tin compounds are added to the support material in an amount sufficient to incorporate therein from about 0.01 to 5 weight percent of tin, based on weight of support. Normally the tin compound will be present in an amount in the range of about 0.1 to about 2 weight percent of support calculated as tin metal.

In the practice of the present invention the reforming zone can be operated over a wide range of reaction conditions. Generally, the temperature is in the range of from about 750° to about 1250° F., the pressure is in the range of from about 0 to about 500 psig, the amount of steam employed is in the range of from about 0.5 to about 30 moles per mole of feedstock, and the feedstock rate expressed as liquid hourly space velocity (LHSV) is in the range of from about 0.2 to about 10. Good results have been obtained employing a temperature in the range of from about 900° to 1100° F., a pressure in the range of from about 50 to about 300 psig, an amount of steam in the range of from about 2.5 to about 15 moles per mol of feedstock, and a feedstock rate in the range of from about 0.5 to about 5 LHSV.

Also the selective hydrogenation zone can be operated over a wide range of reaction conditions. Generally the temperature is in the range of from 300° to about 800° F., the pressure is in the range of from about 0 to about 500 psig, the amount of steam employed is in the range from about 2 to about 50 mols per mole of feedstock, the amount of hydrogen employed is in the range from about 0.2 to about 5 mols per mol of feedstock, and the feedstock rate expressed in terms of liquid hourly space velocity (LHSV) is in the range of from about 0.4 to about 20. Good results have been obtained employing a temperature in the range of from about 500° to about 800° F, a pressure in the range of from about 50 to about 300 psig, an amount of steam in the range of from about 5 to about 25 mols per mol of feedstock, an amount of hydrogen in the range of from about 0.5 to about 3 mols per mol of feedstock, and a feedstock rate expressed in terms of liquid hourly space velocity (LHSV) in the range of from about 0.5 to about 15.

In the practice of the present invention the reforming reaction produces hydrogen which is generally sufficient in amount to preclude the necessity for the addition of hydrogen during the subsequent selective hydrogenation reaction; however, in some instance additional hydrogen may be desirable. Usually the selective hydrogenation zone is operated at a temperature in the range of from about 200° to about 400° F. lower than the reforming zone. In one embodiment of the invention the entire product produced in the reforming zone is contacted with water prior to being passed to the selective hydrogenation zone. This contacting with water quenches the effluent feedstream to a temperature suitable for selective hydrogenation, and the resulting mixture comprising olefinic hydrocarbons having more than one double bond, steam and hydrogen is passed to the selective hydrogenation zone.

Catalysts suitable for use in accordance with the present invention are disclosed in U.S. Pat. No. 3,692,701 issued to E. O. Box on Sept. 19, 1972 on application Ser. No. 55,213, filed July 15, 1970.

It is also noted that one of the advantages of the present invention, particularly from a practical standpoint, is that the same catalyst can be used in both the reforming and selective hydrogenation zones. This precludes maintaining an inventory of a different catalyst for each zone.

In an effort to better illustrate the present invention the following examples are provided.

EXAMPLE I

A zinc aluminate spinel support containing 1 wt. % tin was prepared by mixing 1700 gm flame-hydrolyzed $Al_2O_3$ with 9 liters of deionized water. To the stirred mixture was added 1450 gm. of powdered ZnO and 40 gm. of powdered stannic oxide. The mixture was divided into two portions. Each portion was ball milled for about one hour, the portions were recombined, stirred for 20 minutes to mix the portions together, and the mixture was dried at 110° C. The dried mixture was ground and screened to pass a 40 mesh screen. A portion of the mixture was formed into ¼ inch tablets and calcined for 1 hour at each of the following temperatures, 800° F., 1000° F., and 1100° F.; then the tablets were calcined for an additional 3 hours at 1850° F. The calcined material was ground and screened to obtain 20–40 mesh particles having an apparent bulk density of 0.86 gm/cc. The particles were impregnated with sufficient aqueous chloroplatinic acid to give 0.4 wt. % platinum based on the weight of the final composite, dried under a heat lamp and calcined at 1050° F. for 3-4 hours.

A series of runs was made employing the above catalyst to reform n-heptane to prepare a feedstock suitable for selective hydrogenation in accordance with the invention.

A laboratory reactor was charged with 44.5 gm. (47 cc.) of the prepared catalyst and the reactor was brought up to operating temperature. The feedstock passed over the catalyst under reaction conditions was n-heptane at a rate of about 80 cc/hour or 1.7 liquid hourly space velocity (LHSV). The reaction conditions consisted of: reactor temperator 1020° F., reactor pressure—100 psig, and a steam rate of about 5:1 mole ratio based on the hydrocarbon feed. The process was conducted over several days in a cyclic fashion consisting of bringing the reactor up to temperature, flushing the catalyst with nitrogen for 5 minutes at a rate of about 1–1.5 liters/hour, passing air for 20 minutes at the rate of 10–11 liters/hour over the catalyst followed by another 5 minute nitrogen purge to give a 30 minute regeneration cycle. The feed was contacted with the catalyst for 1.5 hours, then the regeneration cycle was resumed. A total of 40 such total cycles was run (40 regeneration and 40 process) giving a catalyst age of 80 hours at the conclusion of the runs. The effluent from each day's run was collected and analyzed by gas-liquid chromatography. Typical results, calculated on a dry basis, for Runs 1 and 2, made under differing feed rates, are presented in Table 1.

Table 1
DEHYDROGENATION OF n-HEPTANE

|  | Run 1 | Run 2 |
|---|---|---|
| Number of Cycles | 4 | 4 |
| Feed Rate; LHSV | 1.65 | 3.23 |
| Steam:Hydrocarbon Mole Ratio | 5.27 | 5.41 |
| Conversion, % | 52.0 | 31.9 |

The product compositions in mole % are given in Table 2.

Table 2
PRODUCT COMPOSITION, MOLE %

|  | 1 | | | 2 | | |
|---|---|---|---|---|---|---|
| Run | Gas (net) | Liquid (Observed) | Total | Gas (Net) | Liquid (Observed) | Total |
| Hydrogen | 87.89 | — | 56.14 | 92.92 | — | 45.37 |
| Carbon Monoxide | 0.00 | — | 0.00 | 0.06 | — | 0.03 |
| Carbon Dioxide | 1.40 | — | 0.89 | 1.27 | — | 0.62 |
| Methane | 1.56 | — | 1.00 | 1.23 | — | 0.60 |
| Ethane/Ethylene | 2.48 | 0.00 | 1.58 | 1.67 | 0.00 | 0.81 |
| Propane | 1.22 | 0.06 | 0.80 | 0.36 | 0.04 | 0.20 |
| Propylene | 0.54 | 0.00 | 0.34 | 0.53 | 0.00 | 0.26 |
| Butane | 0.55 | 0.21 | 0.43 | 0.12 | 0.06 | 0.09 |
| Butenes | 1.50 | 0.15 | 1.01 | 0.29 | 0.05 | 0.17 |
| Pentane | 0.42 | 0.33 | 0.38 | 0.00 | 0.06 | 0.03 |
| Pentenes | 0.48 | 0.08 | 0.33 | 0.20 | 0.05 | 0.12 |
| Hexane | 0.24 | 0.11 | 0.19 | 0.01 | 0.03 | 0.02 |
| Hexenes | 0.28 | 0.11 | 0.22 | 0.00 | 0.07 | 0.03 |
| Isoheptanes | 0.40 | 0.38 | 0.39 | 0.17 | 0.09 | 0.13 |
| n-Heptane | 0.70 | 51.28 | 18.88 | 0.88 | 69.05 | 35.51 |
| Heptenes | 0.11 | 8.69 | 3.19 | 0.13 | 10.78 | 5.54 |
| Heptadienes | 0.01 | 1.16 | 0.42 | 0.01 | 1.26 | 0.65 |
| Benzene | 0.01 | 0.58 | 0.21 | 0.01 | 0.60 | 0.31 |
| Toluene | 0.12 | 36.26 | 13.11 | 0.05 | 17.79 | 9.06 |
| Xylenes | 0.00 | 0.53 | 0.19 | 0.00 | 0.00 |  |
| Coke | — | — | 0.19 | — | — | 0.37 |
| $H_2$, SCF/barrel |  | 1289.2 |  |  |  |  |

The liquid hydrocarbons from all the runs made during the dehydrogenation of n-heptane were collected to form a composite sample which was used as a feedstock in various subsequent selective hydrogenation runs.

EXAMPLE II

Three catalysts were prepared and used according to the invention to selectively hydrogenate the diolefins in the composite sample which were formed in the process described in Example I. The catalysts were prepared as follows:

Catalyst A: A portion of the Pt/Sn/ZnAl$_2$O$_4$ catalyst was taken from the reactor at the end of the last run in Example I for this purpose.

Catalyst B: Calcined zinc aluminate particles prepared as described in Example I were impregnated with sufficient aqueous palladium nitrate solution to give 0.5 wt. % palladium based on the weight of the composite. The mixture was dried at 230° F. for 2 hours and then calcined at 1050° F. for 3 hours.

Catalyst C: A 25 wt. % Ni$_3$(AsO$_4$)$_2$ on flame hydrolyzed alumina catalyst was prepared by slurrying 150 g alumina in a solution of 88.0 gms NiSO$_4$.6H$_2$O dissolved in 1200 cc of distilled water. H$_3$AsO$_4$ dissolved in 300 cc of distilled water was added with stirring to the slurry.

After stirring for 15 minutes, dilute ammonium hydroxide was added to a pH of 8.0 and the mixture was filtered. The solid material was dried overnight in an oven at 212° F. It was ground and screened to 10–20 mesh. The catalyst had an arsenic content (calculated) of 8.6 wt. %.

The feed composition employed is shown in Table 3 below.

Table 3

| Feed Composition, Mole % | |
|---|---|
| propylene to hexenes | 0.87 |
| n-heptane | 61.26 |
| heptenes | 10.16 |
| heptadienes | 1.42 |
| benzene | 0.43 |
| toluene | 25.71 |
| xylenes | 0.15 |

The effectiveness of Catalysts A, B and C as selective hydrogenation catalysts for the liquid composite feedstock above was determined as follows:

The reactor was charged with 10 cc of the catalyst to be tested. Catalyst A was tested in two series of runs at two different temperatures. Catalyst B was tested in a single series of runs at a third temperature and Catalyst C was tested in two series of runs at the same temperature. Each series of runs was conducted for several days. With Catalyst A, the process was conducted about 6 hours per day with one 30 minute regeneration period. The total catalyst time, including regenerations, amounted to 54.2 hours for Catalyst A. Catalyst B was treated in a similar fashion and its time amounted to 55.1 hours. Catalyst C was also tested over a period of several days to give a time of 20.3 hours. The operating conditions and the results of the runs are presented in Tables 4 and 5.

Table 4
SELECTIVE HYDROGENATION TESTING

|  | A | | B | C | |
|---|---|---|---|---|---|
| Catalyst | Run 3 | Run 4 | Run 5 | Run 6 | Run 7 |
| Reactor Temp. °F. | 800 | 700 | 600 | 700 | 700 |
| Reactor Press. psig | 100 | 100 | 100 | 100 | 100 |
| Feed LHSV | 2.0 | 2.0 | 1.9 | 3.9 | 7.9 |

Table 4-continued

| SELECTIVE HYDROGENATION TESTING | | | | | |
|---|---|---|---|---|---|
| | A | | B | C | |
| Catalyst | Run 3 | Run 4 | Run 5 | Run 6 | Run 7 |
| Steam/Feed Mole Ratio | 9.9 | 9.9 | 10.4 | 10.8 | 10.2 |
| $H_2$/Feed Mole Ratio | 1.4 | 1.4 | 1.3 | 1.4 | 1.4 |
| % Dienes by M.A.V.[1] | 0.31 | 0.13 | ND[3] | ND[3] | ND[3] |
| % Dienes by GLC[2] | 0.39 | 0.40 | 0.24 | 0.23 | 0.27 |
| % Dienes Removed (GLC)[4] | 74 | 76 | 85 | 84 | 81 |
| % n-Heptane recovered | 90.0[5] | 91.5[5] | 99.0 | 99.0 | 100.7 |
| % Heptenes recovered | 66.4[5] | 50.8[5] | 108.0 | 101.1 | 105.8 |
| % Toluene recovered | 97.8 | 100.0 | 102.3 | 99.3 | 99.3 |

[1]In separator liquid product. (M.A.V. is maleic anhydride value)
[2]In separator liquid product by gas-liquid chromatography.
[3]Not determined.
[4]GLC peaks measured as dienes probably contain some non-dienes. Actual diene removal is thought to be higher.
[5]Some losses incurred due to thermal cracking in vaporizer ahead of reactor.

Table 5

| PRODUCT COMPOSITION, Mole % | | | | | |
|---|---|---|---|---|---|
| | A | | B | C | |
| | Run 3 | Run 4 | Run 5 | Run 6 | Run 7 |
| Propylene to hexenes | 7.46 | 13.59 | 3.58 | 0.52 | 0.88 |
| iso-heptane | 0.51 | 0.33 | 0.41 | 0.23 | 0.20 |
| n-heptane | 59.40 | 55.00 | 59.50 | 61.51 | 61.95 |
| heptenes | 6.66 | 5.04 | 10.80 | 11.38 | 10.77 |
| heptadienes | 0.37 | 0.36 | 0.23 | 0.22 | 0.27 |
| benzene | 0.51 | 0.58 | 0.49 | 0.29 | 0.32 |
| toluene | 25.00 | 25.10 | 25.79 | 25.85 | 25.70 |
| xylenes | Trace | Trace | Trace | Trace | Trace |

The results show that the catalyst prepared with Group VIII metals such as platinum, palladium and nickel are effective in the selective hydrogenation of diolefins according to the present invention. In particular, the mole percent of diolefins in the feed was reduced from 1.42 to 0.37, 0.36, 0.23, 0.22 and 0.27 in Runs 3, 4, 5, 6 and 7 respectively.

I claim:

1. A process comprising:
contacting a feedstock with a first catalyst in a first zone in the presence of steam under conditions to reform said feedstock to produce a reformate comprising olefins and diolefins, said feedstock comprising paraffin and cycloparaffin hydrocarbons, said first catalyst comprising a Group VIII metal or an oxide thereof on a carrier comprising a Group II metal aluminate spinel containing tin or an oxide of tin; and contacting said reformate with a second catalyst in a second zone in the presence of steam and hydrogen and under hydrogenating conditions to selectively hydrogenate said diolefins contained in said reformate to reduce the unsaturation thereof, said second catalyst consisting essentially of a Group VIII metal or an oxide thereof on a carrier comprising a Group II metal aluminate spinel containing tin or an oxide of tin.

2. The process of claim 1 wherein the catalyst in each of said zones comprises the Group VIII metal in an amount in the range of from about 0.1 to about 5 weight percent based on weight of the support in each respective zone and comprises the tin metal in an amount in the range of from about 0.01 to about 5 weight percent based on weight of the support in each respective zone and the paraffin and cycloparaffin hydrocarbon feedstock contains from about 6 to about 20 carbon atoms per molecule.

3. The process of claim 2 wherein the catalyst in each of said zones comprises the Group VIII metal in an amount in the range of from about 0.1 to 1 weight percent based on weight of the support in each respective zone and consists of the tin metal in an amount in the range of from about 0.1 to about 2 weight percent based on weight of the support in each respective zone and the paraffin and cycloparaffin hydrocarbon feedstock contains from about 6 to about 12 carbon atoms per molecule.

4. The process of claim 1 wherein the steam in said first zone is present in an amount in the range of from about 0.5 to about 30 moles of steam per mole of feedstock, the steam in said second zone is present in an amount in the range of from about 2 to about 50 moles of steam per mole of reformate and the hydrogen in said second zone is present in an amount in the range of from about 0.2 to about 5 moles of hydrogen per mole of reformate.

5. The process of claim 4 wherein the steam in said first zone is present in an amount in the range of from about 2.5 to about 15 moles of steam per mole of feedstock, the steam in said second zone is present in an amount in the range of from about 5 to about 30 moles of steam per mole of reformate and the hydrogen in said second zone is present in an amount in the range of from about 0.5 to about 3 moles of hydrogen per mole of reformate.

6. The process of claim 1 wherein the reforming reaction of zone 1 is carried out at a temperature in the range of from about 750° to 1250° F., at a pressure in the range of from about 0 to about 500 psig, and at a liquid hourly space velocity in the range of from about 0.2 to 10, and the selective hydrogenation reaction of zone 2 is carried out at a temperature in the range of from about 300° to about 800° F., at a pressure in the range of from about 0 to about 500 psig and at a liquid hourly space velocity of from about 0.4 to about 20.

7. The process of claim 6 wherein the reforming reaction of zone 1 is carried out at a temperature in the range of from about 900° to about 1100° F., at a pressure in the range of from about 50 to about 300 psig, and at a liquid hourly space velocity in the range of from about 0.5 to about 5, and the selective hydrogenation reaction of zone 2 is carried out at a temperature in the range of from about 500° to about 800° F., at a pressure in the range of from about 50 to about 300 psig and at a liquid hourly space velocity of from about 0.5 to about 15.

8. The process of claim 1 wherein the same catalyst of zone 1 is used in zone 2.

9. The process of claim 1 wherein the Group VIII metal is selected from the group consisting of nickel, platinum, ruthenium, palladium, iridium, osmium, and mixtures thereof.

10. The process of claim 1 wherein the Group VIII metal is selected from the group consisting of platinum and palladium and the Group II metal aluminate spinel is zinc aluminate.

* * * * *